(12) United States Patent
Hupfield

(10) Patent No.: US 7,019,098 B2
(45) Date of Patent: Mar. 28, 2006

(54) POLYSILOXANES AND GELS AND PASTES CONTAINING THEM

(75) Inventor: Peter Cheshire Hupfield, Trevaughan (GB)

(73) Assignee: Dow Corning Limited, (GB)

( * ) Notice: Subject to any disclaimer, the term of this patent is extended or adjusted under 35 U.S.C. 154(b) by 0 days.

(21) Appl. No.: 10/477,508

(22) PCT Filed: May 14, 2002

(86) PCT No.: PCT/EP02/06447

§ 371 (c)(1),
(2), (4) Date: Nov. 12, 2003

(87) PCT Pub. No.: WO02/094937

PCT Pub. Date: Nov. 28, 2002

(65) Prior Publication Data

US 2004/0147670 A1    Jul. 29, 2004

(30) Foreign Application Priority Data

May 23, 2001  (GB) .................................... 0112525

(51) Int. Cl.
*C08G 77/06*  (2006.01)
(52) U.S. Cl. .............................. 528/31; 528/25; 528/26
(58) Field of Classification Search .................. 528/25, 528/26, 31, 42
See application file for complete search history.

(56) References Cited

U.S. PATENT DOCUMENTS

| 4,725,658 | A |   | 2/1988  | Thayer et al. |
| 5,334,737 | A |   | 8/1994  | Thimineur et al. |
| 5,482,775 | A | * | 1/1996  | Miyabayashi ................ 428/391 |
| 5,654,362 | A |   | 8/1997  | Schulz, Jr. et al. |
| 5,889,108 | A |   | 3/1999  | Zhang |
| 5,977,280 | A | * | 11/1999 | Kadlec et al. ................. 528/15 |
| 6,200,581 | B1|   | 3/2001  | Lin et al. |
| 6,770,708 | B1| * | 8/2004  | Kadlec et al. ............... 524/588 |
| 6,822,066 | B1| * | 11/2004 | Gordon et al. ................ 528/25 |

FOREIGN PATENT DOCUMENTS

| EP | 848029    | 6/1998 |
| EP | 934959    | 8/1999 |
| JP | A-1-217040| 8/1989 |

* cited by examiner

*Primary Examiner*—Marc S Zimmer
(74) *Attorney, Agent, or Firm*—Robert L. McKellar; McKellar IP Law, PLLC

(57) ABSTRACT

A crosslinked polysiloxane comprises polysiloxane chains substituted by an ester-containing organic moiety joined by crosslinks derived from the reaction of an alpha, omega-diunsaturated hydrocarbon or fluorohydrocarbon with Si—H groups on the polysiloxane chains. The ester-containing organic moiety has the formula -A-COOR where A is an alkylene linkage having 1–18 carbon atoms which is optionally fluoro-substituted and R is an alkyl or fluoroalkyl group. The crosslinked polysiloxane can form an elastomeric gel in a liquid organic or silicone material, which is useful in preparing cosmetics.

11 Claims, No Drawings

POLYSILOXANES AND GELS AND PASTES CONTAINING THEM

This invention is directed to crosslinked polyorganosiloxanes, and to low molecular weight siloxane fluids or solvents swollen into silicone gels incorporating the crosslinked polyorganosiloxanes. The silicone gels, and silicone pastes derived from them, are useful in cosmetic preparations.

U.S. Pat. No. 5,654,362 describes silicone gels made by reacting an Si—H containing polysiloxane with an alpha, omega-diene. The reaction is conducted in the presence of a platinum catalyst and in the presence of a low molecular weight silicone oil. The reaction is continued until a gel is formed by crosslinking and addition of Si—H across double bonds in the alpha, omega-diene. When additional amounts of low molecular weight silicone oil are added to the gel, and the silicone oil and the gel are subjected to shear force, a silicone paste can be formed.

U.S. Pat. No. 5,811,487 describes a modified process in which the SiH siloxane is first partially reacted with a mono-alkenyl functionalized polyether and is then crosslinked by the alpha, omega-diene.

U.S. Pat. No. 5,889,108 describes low molecular weight siloxane fluids thickened by silicone elastomers made by combining in one pot an Si—H containing siloxane, a mono-alkenyl polyether, an alpha, omega-diene, and a low molecular weight siloxane fluid.

U.S. Pat. No. 6,200,581-B1 describes an elastomeric silicone terpolymer composition obtainable by combining and reacting a Si—H containing polysiloxane, a mono-alkenyl polyether, an α-olefin containing at least ten carbon atoms, an α,ω-unsaturated hydrocarbon and a platinum catalyst in the presence of an oil which is selected from organic compounds and/or compounds containing a silicon atom, and continuing the reaction until there is formed a crosslinked three-dimensional gelled network of an elastomeric silicone terpolymer.

According to the present invention a crosslinked polysiloxane comprises polysiloxane chains substituted by an ester-substituted organic moiety and joined by crosslinks derived from the reaction of an alpha, omega-diunsaturated hydrocarbon or fluorohydrocarbon with Si—H groups on the polysiloxane chains. The invention also includes an elastomeric gel comprising such a crosslinked polysiloxane in a liquid organic or silicone material and to processes for making the gel, and to a cosmetic preparation comprising a paste which comprises such a crosslinked polyorganosiloxane.

The ester-substituted organic moiety preferably has the formula -A-COOR where A is an alkylene linkage having 1–18 carbon atoms which is optionally fluoro-substituted and R is an alkyl or fluoroalkyl group. R can for example be an alkyl group having 1–18 carbon atoms, preferably 1 to 4 carbon atoms, or can be a fluoroalkyl group, for example an alkyl group containing 1–20 carbon atoms substituted by 1–41 fluorine atoms. The ester-substituted organic moiety can alternatively be of the formula -A-OOC—R, in which A and R are defined as above. In cosmetics containing silicones, particularly skin preparations, the ester-functional crosslinked polysiloxanes provide improved emollient properties.

Where R is a fluoroalkyl group, it preferably has the formula —(CH2)mRf, where m=0–3 and Rf is a fluoroalkyl group. One preferred type of fluoroalkyl group has the formula —(CH2)mCnF2n+1, where A is an alkylene linkage having 1–18 carbon atoms which is optionally fluoro-substituted and n=1–18. Examples of the group (CH2)mCnF2n+1 include —CH2CH2—C6F13, —CH2CF3, —CH2(CF2)2CF3 and —CH2CH2CF3. An example of a fluoroalkyl ester-containing organic moiety has the formula —(CH2)10—COO—CH2CH2—C6F13. Cosmetics containing fluoroalkyl ester-functional crosslinked polysiloxanes according to the invention, particularly those in which the fluoro-substituent is terminated with a perfluoroalkyl group Rf, have a lighter, more lubricious, satiny skin feel as well as improved emollient properties.

The ester-substituted organic moiety can be introduced into a polyorganohydrogensiloxane by a hydrosilylation reaction between an unsaturated, preferably terminally unsaturated, ester and a polyorganohydrogen siloxane. The polyorganohydrogen siloxane can be represented by compounds of the formula $R_3SiO(R'_2SiO)_a(R''HSiO)_bSiR_3$ designated herein as type $A^1$ and compounds of the formula $HR_2SiO(R'_2SiO)_cSiR_2H$ or formula $HR_2SiO(R'_2SiO)_a(R''HSiO)_bSiR_2H$ designated herein as type $A^2$. In these formulas, R, R', and R'', are alkyl groups with 1–30, preferably 1–6 carbon atoms; a is 0–250; b is 1–250; and c is 0–250. Compounds of either type $A^1$ or $A^2$, or both, can be used in the reaction. The Si—H containing polysiloxane can also comprise an alkylhydrogen cyclosiloxane or an alkylhydrogen-dialkyl cyclosiloxane copolymer, represented in general by the formula $(R'_2SiO)_{a'}(R''HSiO)_{b'}$, where R'' and R' are as defined above and where a' is 0–7 and b' is 3–10. Some representative compounds of these types are (OSiMeH)$_4$, (OSiMeH)$_3$(OSiMeC$_6$H$_{13}$), (OSiMeH)$_2$(OSiMeC$_6$H$_{13}$)$_2$ and (OSiMeH)(OSiMeC$_6$H$_{13}$)$_3$, where Me represents —CH$_3$. The unsaturated ester can for example be of the formula CH2=CH—A'—COOR or CH2=CH—A'—OOC—R, where A' is an alkylene linkage having 1–16 carbon atoms which is optionally fluoro-substituted or a direct bond and R is defined as above.

The above hydrosilylation reaction should generally be carried out with a stoichiometric excess of Si—H groups over vinyl groups so that the resulting ester-substituted polysiloxane contains residual Si—H groups for subsequent reaction according to the invention with an alpha, omega-diunsaturated hydrocarbon or fluorohydrocarbon. The molar ratio of Si—H groups to vinyl groups can for example be 1.25–30:1. The resulting polyorganohydrogensiloxane substituted by an ester-containing organic moiety preferably has ester-containing organic moieties bonded to 3–60%, most preferably 10–30%, of the Si atoms in the polysiloxane.

The hydrosilylation reaction generally needs a catalyst. Suitable catalysts are Group VIII transition metal, particularly platinum, catalysts. One preferred platinum catalyst is a platinum divinyl tetramethyl disiloxane complex typically containing about one weight percent of platinum in a solvent such as toluene. Another preferred platinum catalyst is a reaction product of chloroplatinic acid and an organosilicon compound containing terminal aliphatic unsaturation. The noble metal catalysts is preferably used in amounts from 0.00001–0.5 parts per 100 weight parts of the SiH containing polysiloxane, most preferably 0.00001–0.002 parts.

The polyorganohydrogensiloxane substituted by an ester-containing organic moiety can alternatively be produced by an equilibration reaction between a polyorganohydrogensiloxane and a polyorganosiloxane substituted by an ester-containing organic moiety in the presence of an equilibration catalyst, for example an acid catalyst such as trifluoromethanesulphonic acid or a phosphazene catalyst.

The crosslinked polysiloxane according to the invention is produced by a hydrosilylation reaction between such a polyorganohydrogensiloxane substituted by an ester-containing organic moiety and an alpha, omega-diunsaturated hydrocarbon or fluorohydrocarbon. The most preferred α,ω-unsaturated hydrocarbon is an α,ω-diene of the formula $CH_2=CH(CH_2)_dCH=CH_2$ where d is 1–20. Some representative examples of suitable α,ω-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene and 1,19-eicosadiene. Alternative α,ω-unsaturated hydrocarbons which can be used are α,ω-diynes of the formula CH C(CH$_2$)$_e$C CH; or α,ω-ene-ynes of the formula $CH_2=CH(CH_2)_eC$ CH where e is 0–20. Some representative examples of suitable α,ω-diynes for use herein are 1,3-butadiyne HC C—C CH and 1,5-hexadiyne (dipropargyl) HC C—$CH_2CH_2$—C CH. One example of a suitable α,ω-ene-yne for use herein is hexene-5-yne-1 $CH_2=CHCH_2CH_2C$ CH. Preferred α,ω-unsaturated fluorohydrocarbons have the formula $CH_2=CH-(CH2)x-Z-(CH2)x-CH=CH_2$ where each x=1–10 and Z is a fluoro-substituted alkylene linkage having 1–20 carbon atoms, for example a linkage containing —CF2-units or pendant —CF3 groups.

The use of an alpha, omega-diunsaturated hydrocarbon or fluorohydrocarbon as crosslinker gives more reaction control than an alpha, omega-vinylsiloxane as disclosed in JP-A-00-281791. Since the alpha, omega-diunsaturated hydrocarbon or fluorohydrocarbon is a pure material, it gives performance that is easily modified when it is reacted with a statistical distribution of dimethylsiloxane/methylhydrogensiloxane materials; that is, if we change initial reagent concentration, SiH/vinyl ratios, or cross-link density, we see a much more pronounced effect on final properties than in a system based on networks formed from two statistical distributions of materials. An alpha, omega-diene such as 1,5-hexadiene also leads to a much less process intensive chemistry, as the hexadiene reacts very fast with SiH, and the resulting hexenyl siloxane has much faster kinetics than its vinyl analogue. The process of the present invention does not require intensive processing such as multiple passes through a three or four roll mill.

The hydrosilylation reaction between the polyorganohydrogensiloxane substituted by an ester-containing organic moiety and the alpha, omega-diunsaturated hydrocarbon or fluorohydrocarbon is preferably carried out in a liquid organic or silicone material. The hydrosilylation reaction is carried out in the presence of a catalyst, preferably a Group VIII transition metal, particularly platinum, catalyst as discussed above. The stoichiometric ratio of the substituted polyorganohydrogensiloxane to the alpha, omega-diunsaturated hydrocarbon or fluorohydrocarbon is generally in the range 1:2 to 2:1, preferably about 1:1. When the substituted polyorganohydrogensiloxane contains at least 3 Si—H groups per molecule and the concentration of the reagents in the liquid organic or silicone material is at least 5 or 10% by weight, a gel is generally formed comprising the crosslinked polysiloxane reaction product dispersed throughout the liquid organic or silicone material. Carrying out of the process is simply a matter of mixing the above ingredients, including the catalyst, at room temperature until a gel is formed. Higher temperatures to speed up the process can be used, if desired.

The liquid organic or silicone material is preferably essentially non-reactive and in particular does not react to crosslink the Si—H functional polysiloxane. Most preferably this non-reactive liquid comprises a silicone oil, particularly a low molecular weight linear, branched or cyclic alkyl or aryl siloxane, particularly a methyl siloxane. The non-reactive liquid can be volatile or non-volatile. Linear volatile methyl siloxanes have the formula $(CH_3)_3SiO$ $\{(CH_3)_2SiO\}_kSi(CH_3)_3$, where k is 0–5. Cyclic volatile methyl siloxanes have the formula $\{(CH_3)_2SiO\}j$, where j is 4–9. Preferably, these volatile methyl siloxane have a boiling point less than 250° C. and viscosity of 0.65 to 5.0 mm$^2$/s, for example hexamethyldisiloxane, octamethyltrisiloxane, decamethyltetrasiloxane, dodecamethylpentasiloxane, tetradecamethylhexasiloxane or hexadecamethylheptasiloxane, octamethylcyclotetrasiloxane, decamethylcyclopentasiloxane or dodecamethylcyclohexasiloxane, heptamethyl-3-{(trimethylsilyl)oxy}-trisiloxane ($M_3T$), hexamethyl-3,3,bis {(trimethylsilyl)oxy} trisiloxane ($M_4Q$) or pentamethyl {(trimethylsilyl)oxy} cyclotrisiloxane. Non-volatile polysiloxanes, typically having a viscosity in the range 5–375 mPa.s, can additionally or alternatively be used.

Liquid organic compounds which can be present include aromatic hydrocarbons such as benzene, toluene, ethylbenzene or xylene, aliphatic hydrocarbons such as pentane, cyclohexane, heptane or mineral spirits or petroleum hydrocarbons such as petroleum jelly, mineral oil, gasoline, naphtha, kerosene, gas oil, heavy oil or crude oil, alcohols such as methanol, ethanol, 1-propanol, cyclohexanol, benzyl alcohol, 2-octanol, ethylene glycol, propylene glycol or glycerol, aldehydes, ketones such as acetone, methyl ethyl ketone, cyclohexanone, diacetone alcohol, methyl amyl ketone and diisobutyl ketone, amines, esters such as ethyl acetate, isopropyl acetate, ethyl acetoacetate, amyl acetate, isobutyl isobutyrate, benzyl acetate or isopropyl palmitate, ethers such as ethyl ether, n-butyl ether, tetrahydrofuran and 1,4-dioxane, glycol ethers such as ethylene glycol monomethyl ether, ethylene glycol monomethyl ether acetate, diethylene glycol monobutyl ether or propylene glycol monophenyl ether, alkyl halides such as chloroform, carbon tetrachloride, perchloroethylene, ethyl chloride or chlorobenzene, or aromatic halides. Some of these organic compounds such as alcohols or aldehydes may react with Si—H groups, but they are less reactive towards Si—H groups than are vinyl groups and they can be regarded as essentially non-reactive. Alternatively the liquid organic compound can be a lubricating oil such as spindle oil or turbine oil, or a fatty oil such as corn oil, soybean oil, olive oil, rape seed oil, cotton seed oil, sardine oil, herring oil or whale oil, or acetonitrile, nitromethane, dimethylformamide, propylene oxide, trioctyl phosphate, butyrolactone, furfural, pine oil, turpentine and m-cresol.

The non-reactive liquid can comprise a volatile flavouring agent such as oil of wintergreen, peppermint oil, spearmint oil, menthol, vanilla, cinnamon oil, clove oil, bay oil, anise oil, eucalyptus oil, thyme oil, cedar leaf oil, oil of nutmeg, oil of sage, cassia oil, cocoa, liquorice, high fructose corn syrup, a citrus oil such as lemon, orange, lime and grapefruit, a fruit essence such as apple, pear, peach, grape, strawberry, raspberry, cherry, plum, pineapple and apricot, cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal or 2-ethyl butyraldehyde. Additionally or alternatively the non-reactive liquid can include a volatile fragrance such as a natural product or perfume oil, for example ambergris, benzoin, civet, clove, leaf oil, jasmine, mimosa, musk, myrrh, orris, sandalwood oil or vetivert oil, or an aroma chemical such as amyl salicylate, amyl cinnamic aldehyde, benzyl acetate, citronellol, coumarin, geraniol, isobornyl acetate, ambrette or terpinyl acetate, or a classic family perfume oil such as the floral bouquet family, the oriental family, the chypre family, the woody family, the citrus family, the canoe family, the leather family, the spice family or the herbal family.

One process according to the invention for the preparation of an elastomeric gel comprises reacting a polyorganohydrogensiloxane (A) having at least 3 Si—H groups per molecule with an unsaturated ester (B), preferably of the formula CH2=CH-A'-COOR or CH2=CH-A'-OOC—R defined as above, and an alpha, omega-diunsaturated hydrocarbon or fluorohydrocarbon (C), at least the reaction between (A) and (C) taking place in a non-reactive liquid organic or silicone material. The polyorganohydrogensiloxane (A) can be reacted with the unsaturated ester (B) and then with the alpha, omega-diunsaturated hydrocarbon or fluorohydrocarbon (C), as described above. Alternatively the polyorganohydrogensiloxane (A) can be reacted with the unsaturated ester (B) and the alpha, omega-diunsaturated hydrocarbon or fluorohydrocarbon (C) together. In this alternative process the hydrosilylation reaction between (A) and (B), forming polysiloxane chains substituted by an ester-containing organic moiety, proceeds simultaneously with the crosslinking hydrosilylation reaction between (A) and (C). The reaction is preferably carried out in a non-reactive liquid organic or silicone material to form a gel comprising the crosslinked polysiloxane reaction product dispersed in the non-reactive liquid organic or silicone material.

A paste can be formed by applying high shear to the gel either as it is being formed or after, preferably in the presence of additional amounts of non-reactive liquid organic or silicone material. Any type of mixing and shearing equipment can be used to form the paste, such as a batch mixer, planetary mixer, single or multiple screw extruder, dynamic or static mixer, colloid mill, homogenizer, sonolator, or a combination thereof.

Active cosmetic or pharmaceutical ingredients can be present during the above reaction or mixing steps for forming the gel or paste, for example oil-soluble vitamins such as Vitamin $A_1$ (Retinol, including trans-retinol, 13-cis-retinol, 11-cis-retinol, 9-cis-retinol and 3,4-didehydro-retinol), $C_2$–$C_{18}$ esters of Retinol such as retinyl acetate, palmitate or propionate, vitamin E, (Tocopherol), or esters of vitamin E such as tocopheryl acetae, linoleate, nicotinate or succinate or mixtures thereof, or water-soluble vitamins such as Vitamin C, Vitamin $B_1$, Vitamin $B_2$, Vitamin $B_6$, Vitamin $B_{12}$, niacin, folic acid, biotin or pantothenic acid , or ascorbyl dipalmitate, palmitate or stearate or ascorbyl methylsilanol pectinate. The vitamin can be used in the composition of the invention in amounts of from 0.01 to 50 percent by weight.

Other types of active ingredients which can be present are drugs, for example water-soluble drugs such as hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin or mebendazole, or oil-soluble drugs such as clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate or steroids. Other pharmaceutical active materials which can be present include antiacne agents such as benzoyl peroxide, triclosan or tretinoin, antibacterial agents such as chlorohexadiene gluconate, antifungal agents such as miconazole nitrate, anti-inflammatory agents such as salicylic acid, corticosteroidal drugs, non-steroidal anti-inflammatory agents such as diclofenac, antipsoriasis agents such as clobetasol propionate or retinoids, anaesthetic agents such as lidocaine, antipruritic agents, antidermatitis agents, and/or agents generally considered barrier films.

The gels and pastes are useful as carriers in antiperspirants and deodorants, or as additives in skin creams, skin care lotions, moisturisers, acne or wrinkle removers, cleansers, bath oils, perfumes, colognes, sachets, sunscreens, pre-shave lotions, after-shave lotions, liquid soaps, shaving soaps, and shaving lathers. They are also useful as agents for enhancing gloss, drying time and/or condition in hair shampoos, hair conditioners, hair sprays, mousses, permanents, depilatories and cuticle coats or as levelling and spreading agents for pigments in make-up, colour cosmetics, foundations, blushes, lipsticks, lip balms, eyeliners, mascaras, oil removers, cosmetic removers and powders. More generally they are useful as delivery systems for oil and water soluble substances (e.g. vitamins), as carriers for pharmaceuticals, biocides, herbicides, pesticides and other biologically active compounds, as agents for incorporating water and water-soluble substances (e.g. salicylic acid, glycerol, enzymes or glycolic acid) in hydrophobic systems, as fillers or insulation materials for electric cables, as a soil or water barrier for in-ground stabilisation, as a replacement for epoxy materials used in coil-on plugs designs in the electrics industry. The pastes can be used as a carrier for crosslinked silicone rubber particles to either provide for easier incorporation of the particles into sealants, paints, coatings, greases, adhesives, antifoams, and potting compositions or to act as modifiers of the rheological, physical or energy absorbing properties of the final composition. The pastes have a wide viscosity range and an excellent combination of properties including clarity, thixotropy and shear thinning. They spread smoothly on the skin with an emollient effect. Pastes in which the ester-containing substituent includes a fluoroalkyl group additionally provide a light more lubricious, satiny skin feel. The pastes are particularly useful in antiperspirants and deodorants. A soft solid antiperspirant can be endowed with a thick, satiny, cushion-like feel and benefit from the soft, dry properties of volatile silicones without any greasy sensation.

The invention is illustrated by the following Examples

EXAMPLE 1

A methylhydrogenpolysiloxane (50.63 g) with the following structure, $Me_3SiO(SiMe_2O)90(SiHMe)11SiMe_3$ ($MD_{90}D^{(H)}_{11}M$), was placed into a 500 ml glass jar with a magnetic stirrer bar. To this was added cyclodecamethylpentasiloxane (D5) (45.8 g) and ethyl-10-undecenoate (7.088 g). The reaction mixture was then placed and stirred in a water bath at 70° C. A platinum divinyl tetramethyl disiloxane complex catalyst (Karstedt's catalyst, 0.35 ml) was then charged to the reaction mixture at 70° C. and then held at this temperature for 30 minutes. 1H NMR analysis indicated complete addition of the ethyl-10-undecenoate to the siloxane backbone. To the reaction mixture was added further D5 (315 g) and catalyst (0.35 ml) followed by 1,5-hexadiene (1.78 g) once the reaction mixture was at 70° C. The jar contents were then rapidly stirred resulting in the formation of a cross-linked gel after approximately ten minutes. The crosslinked gel was the placed in an oven for a further three hours at 70° C. yielded a silicone-ester elastomer gel at an elastomer content of 14%.

EXAMPLES 2–5

The elastomer gel prepared in Example 1 was allowed to cool to room temperature upon which it was sheared with D5 to yield a range of materials with varying elastomer contents, and their viscosity measured (Table 1).

TABLE 1

| Example | Elastomer Content (%) | Gel Weight (g) | Weight D5 cyclics (g) | Weight Quencher (g) | Viscosity (Cts) |
|---|---|---|---|---|---|
| 2 | 6 | 42.98 | 57.15 | 0.30 | 1,382[b] |
| 3 | 8 | 57.46 | 43.32 | 0.42 | 141,000[a] |
| 4 | 10 | 71.26 | 28.66 | 0.51 | 446,833[a] |
| 5 | 12 | 85.85 | 14.35 | 0.61 | 789,000[a] |

The viscosities shown in Tables 1 to 6 were measured with either a T Bar (E) spindle at 2.5 RPM using a Helipath (denoted [a]) or with an LV 3 spindle at 100 RPM (denoted [b])

EXAMPLE 6

A methylhydrogenpolysiloxane (50.17 g) with the following structure, $MD_{96}D^{(H)}{}_{14}M$, was placed into a 500 ml glass jar with a magnetic stirrer bar. To this was added D5 (44.8 g) and ethyl-10-undecenoate (10.47 g). The reaction mixture was then placed and stirred in a water bath at 70° C. Karstedt's catalyst (0.35 ml) was then charged to the reaction mixture at 70° C. and then held at this temperature for 30 minutes. $^1$H NMR analysis indicated complete addition of the ethyl-10-undecenoate to the siloxane backbone. To the reaction mixture was added further D5 (338 g) and catalyst (0.35 ml) followed by 1,5-hexadiene (1.77 g) once the reaction mixture was at 70° C. The jar contents were then rapidly stirred resulting in the formation of a cross-linked gel after approximately fifteen minutes. The crosslinked gel was the placed in an oven for a further three hours at 70° C. yielded a silicone-ester elastomer gel at an elastomer content of 14%.

EXAMPLES 7–10

The elastomer gel was allowed to cool to room temperature upon which it was sheared with D5 to yield a range of materials with varying elastomer contents, and their viscosity measured (Table 2).

TABLE 2

| Example | Elastomer Content (%) | Gel Weight (g) | Weight D5 cyclics (g) | Weight Quencher (g) | Viscosity (Cts) |
|---|---|---|---|---|---|
| 7 | 6 | 42.95 | 57.08 | 0.31 | 768[b] |
| 8 | 8 | 57.41 | 43.35 | 0.45 | 105,000[a] |
| 9 | 10 | 71.36 | 28.55 | 0.51 | 372,000[a] |
| 10 | 12 | 85.55 | 14.39 | 0.65 | 680,000[a] |

EXAMPLE 11

A polydimethylsiloxane (50.86 g) with the following structure, $MD_{86}D^{(H)}{}_{18}M$, was placed into a 500 ml glass jar with a magnetic stirrer bar. To this was added D5 (47.8 g) and ethyl-10-undecenoate (16.49 g). The reaction mixture was then placed and stirred in a water bath at 70° C. Karstedt's catalyst (0.35 ml) was then charged to the reaction mixture at 70° C. and then held at this temperature for 30 minutes. $^1$H NMR analysis indicated complete addition of the ethyl-10-undecenoate to the siloxane backbone. To the reaction mixture was added further D5 (377 g) and catalyst (0.35 ml) followed by 1,5-hexadiene (1.78 g) once the reaction mixture was at 70° C. The jar contents were then rapidly stirred resulting in the formation of a cross-linked gel after approximately twenty minutes. The crosslinked gel was the placed in an oven for a further three hours at 70° C. yielded a silicone-ester elastomer gel at an elastomer content of 14%.

EXAMPLES 12–15

The elastomer gel was allowed to cool to room temperature upon which it was sheared with D5 to yield a range of materials with varying elastomer contents, and their viscosity measured (Table 3).

TABLE 3

| Example | Elastomer Content (%) | Gel Weight (g) | Weight D5 cyclics (g) | Weight Quencher (g) | Viscosity (Cts) |
|---|---|---|---|---|---|
| 12 | 6 | 42.86 | 57.16 | 0.31 | 1,536[b] |
| 13 | 8 | 57.43 | 43.36 | 0.44 | 55,500[a] |
| 14 | 10 | 71.55 | 28.56 | 0.53 | 259,000[a] |
| 15 | 12 | 85.53 | 14.38 | 0.64 | 430,000[a] |

EXAMPLE 16

Synthesis of 1H,1H,2H,2H-tridecafluorooctyl-undecylenate

To a round bottomed flask, containing a magnetic stirrer bar, was charged xylene (100 g), 1H,1H,2H,2H-tridecafluorooctanol (50 g) and triethylamine (14 g). The flask contents were then stirred under nitrogen at −10° C. upon which 10-undecenoyl chloride (24.9 g) was added dropwise over a one-hour period. The reaction mixture was then allowed to warm to room temperature upon which it was left overnight. The resulting crude product was then filtered and the Xylene removed under reduced pressure (20 mbar/70° C.). After solvent removal the product was then distilled under reduced pressure (190° C./1 mbar) resulting in a clear liquid obtained in 90% yield.

Preparation of Gel

A SiH-functional polydimethylsiloxane (20.26 g) with the following structure, $Me_3SiO(SiMe_2O)90(SiHMe)11SiMe_3$ was placed into a 500 ml glass jar with a magnetic stirrer bar. To this was added 1H,1H,2H,2H-tridecafluorooctyl-undecylenate (7.088 g) and Karstedt's catalyst (0.3 ml). The reaction mixture was then placed and stirred in a water bath at 70° C. for one hour. $^1$H NMR analysis indicated complete addition of the 1H,1H,2H,2H-tridecafluorooctyl-undecylenate to the siloxane backbone. To the reaction mixture was then added D5 cyclics (166.5 g) and Karstedt's catalyst (0.30 ml) and the mixture was heated. 1,5-hexadiene (0.67 g) was added once the reaction mixture was at 70° C. The jar contents were then rapidly stirred resulting in the formation of a cross-linked gel after approximately ten minutes. The crosslinked gel was then placed in an oven for a further three hours at 70° C. yielding a silicone-fluoroester elastomer gel at an elastomer content of 14%.

EXAMPLES 17–20

The elastomer gel prepared in Example 6 was allowed to cool to room temperature upon which it was sheared with D5 to yield a range of materials with varying elastomer contents, and their viscosity measured (Table 4).

TABLE 4

| Example | Elastomer Content (%) | Gel Weight (g) | Weight D5 cyclics (g) | Weight Quencher (g) | Viscosity (Cts) |
|---|---|---|---|---|---|
| 17 | 6 | 21.4 | 28.6 | 0.15 | 320[b] |
| 18 | 8 | 28.6 | 21.4 | 0.20 | 82,000[a] |
| 19 | 10 | 35.7 | 14.3 | 0.25 | 305,000[a] |
| 20 | 12 | 42.9 | 7.1 | 0.30 | 712,000[a] |

EXAMPLE 21

A Si—H functional polydimethylsiloxane (20.15 g) with the following structure, $Me_3SiO(SiMe_2O)96(SiHMe)14SiMe_3$ was placed into a 500 ml glass jar with a magnetic stirrer bar. To this was added 1H,1H,2H,2H-tridecafluorooctyl-undecylenate (10.40 g) and Karstedt's catalyst (0.3 ml). The reaction mixture was then placed and stirred in a water bath at 70° C. for one hour. $^1H$ NMR analysis indicated complete addition of the 1H,1H,2H,2H-tridecafluorooctyl-undecylenate to the siloxane backbone. To the reaction mixture was then added D5 cyclics (191.8 g) and Karstedt's catalyst (0.30 ml) followed by 1,5-hexadiene (0.67 g) once the reaction mixture was at 70° C. The jar contents were then rapidly stirred resulting in the formation of a cross-linked gel after approximately ten minutes. The crosslinked gel was then placed in an oven for a further three hours at 70° C. yielding a silicone-fluoroester elastomer gel at an elastomer content of 14%.

EXAMPLES 22–25

The elastomer gel prepared in Example 11 was allowed to cool to room temperature upon which it was sheared with D5 to yield a range of materials with varying elastomer contents, and their viscosity measured (Table 5).

TABLE 5

| Example | Elastomer Content (%) | Gel Weight (g) | Weight D5 cyclics (g) | Weight Quencher (g) | Viscosity (Cts) |
|---|---|---|---|---|---|
| 22 | 6 | 21.43 | 28.62 | 0.14 | 230[b] |
| 23 | 8 | 28.62 | 21.38 | 0.19 | 53,500[a] |
| 24 | 10 | 35.60 | 14.40 | 0.24 | 294,000[a] |
| 25 | 12 | 42.90 | 7.10 | 0.29 | 513,000[a] |

EXAMPLE 26

A SiH-functional polydimethylsiloxane (20.15 g) with the following structure, $Me_3SiO(SiMe_2O)86(SiHMe)18SiMe_3$ was placed into a 500 ml glass jar with a magnetic stirrer bar. To this was added 1H,1H,2H,2H-tridecafluorooctyl-undecylenate (16.66 g) and Karstedt's catalyst (0.3 ml). The reaction mixture was then placed and stirred in a water bath at 70° C. for one hour. $^1H$ NMR analysis indicated complete addition of the 1H,1H,2H,2H-tridecafluorooctyl-undecylenate to the siloxane backbone. To the reaction mixture was then added D5 (228.4 g) and Karstedt's catalyst (0.30 ml) followed by 1,5-hexadiene (0.70 g) once the reaction mixture was at 70° C. The jar contents were then rapidly stirred resulting in the formation of a cross-linked gel after approximately ten minutes. The crosslinked gel was then placed in an oven for a further three hours at 70° C. yielding a silicone-fluoroester elastomer gel at an elastomer content of 14%.

EXAMPLES 27–30

The elastomer gel prepared in Example 16 was allowed to cool to room temperature upon which it was sheared with D5 to yield a range of materials with varying elastomer contents, and their viscosity measured (Table 6).

TABLE 6

| Example | Elastomer Content (%) | Gel Weight (g) | Weight D5 cyclics (g) | Weight Quencher (g) | Viscosity (Cts) |
|---|---|---|---|---|---|
| 27 | 6 | 42.86 | 57.16 | 0.31 | 25[b] |
| 28 | 8 | 57.43 | 43.36 | 0.44 | 256[a] |
| 29 | 10 | 71.55 | 28.56 | 0.53 | 19,000[a] |
| 30 | 12 | 85.53 | 14.38 | 0.64 | 151,000[a] |

The invention claimed is:

1. A process for the preparation of an elastomeric gel characterized in that a polyorganohydrogensiloxane (A) having at least 3 Si—H groups per molecule is reacted with an unsaturated ester (B) of the formula —CH$_2$—CH—A'-COOR, wherein A' is selected from the group consisting of (i) an alkylene linkage having 1 to 16 carbon atoms, (ii) fluoro-substituted alkylene linkage, and (iii) a direct bond between the unsaturated moiety and the ester group and R is independently selected from the group consisting of (a) an alkyl group and (b) a fluoroalkyl group, a group (C) that is selected from (c) an alpha, omega-di-unsaturated hydrocarbon and (d) a alpha, omega-di-unsaturated fluorohydrocarbon, wherein at least the reaction between (A) and (C) takes place in a non-reactive material selected from the group consisting of (e) liquid organic material and (f) silicone material.

2. An elastomeric gel prepared by the process of claim 1.

3. A process for the preparation of a paste by shearing a gel according to claim 2.

4. A process for the preparation of an elastomeric gel characterized in that a polyorganohydrogensiloxane having at least 2 Si—H groups per molecule and at least one ester-containing organic substituent per molecule is reacted with an alpha, omega-di-unsaturated fluorohydrocarbon in a material selected from the group consisting of (i) a liquid organic material and (ii) a silicone material.

5. An elastomeric gel prepared by the process of claim 4.

6. A process for the preparation of a paste by shearing a gel according to claim 5.

7. A crosslinked polysiloxane wherein the crosslinked polysiloxane comprises polysiloxane chains substituted by an ester-containing organic moiety joined by crosslinks derived from the reaction of a material selected from the group consisting of (i) an alpha, omega-di-unsaturated hydrocarbon and (ii) alpha, omega-di-unsaturated fluorohydrocarbon with Si—H groups on the polysiloxane chains, wherein the ester-containing organic moieties are bonded to 10 to 30% of the Si atoms in the polysiloxane chain, and wherein the ester-containing organic moieties have the formula -A-COOR wherein A is an alkylene linkage having 1 to 18 carbon atoms and R is independently selected from the group consisting of alkyl and fluoroalkyl groups.

8. A crosslinked polysiloxane according to claim 7 characterized in that R is an alkyl group having 1 to 4 carbon atoms.

9. A crosslinked polysiloxane according to claim 7 characterized in that R is a fluoroalkyl group of the formula $-(CH_2)_m CF_{2n+1}$ where M=0–3 and n=1 to 18.

10. A crosslinked polysiloxane wherein the crosslinked polysiloxane comprises polysiloxane chains substituted by an ester-containing organic moiety joined by crosslinks derived from the reaction of a material selected from the group consisting of (i) alpha, omega-di-unsaturated hydrocarbon and (ii) alpha, omega-di-unsaturated fluorohydrocarbon with Si—H groups on the polysiloxane chains, wherein the ester-containing organic moieties are bonded to 10 to 30% of the Si atoms in the polysiloxane chain, and wherein the ester-containing organic moieties have the formula -A-COOR wherein A is an alkylene linkage comprising fluoroalkyl groups having 1 to 18 carbon atoms and R is independently selected from the group consisting of alkyl and fluoroalkyl groups.

11. A crosslinked polysiloxane according to claim 10 characterized in that the ester-containing organic moiety has the formula $-(CH_2)_{10}-COO-CH_2CH_2-C_6F_{13}-$.

* * * * *